US012490984B2

(12) United States Patent
Saenz Villalobos et al.

(10) Patent No.: US 12,490,984 B2
(45) Date of Patent: Dec. 9, 2025

(54) GRASPING DEVICES, SYSTEMS, AND METHODS FOR TISSUE APPROXIMATION AND APPOSITION

(71) Applicant: Boston Scientific Scimed, Inc., Maple Grove, MN (US)

(72) Inventors: Gonzalo Jose Saenz Villalobos, Alajuela (CR); Deborah Amaya Pineda, Santa Barbara (CR); Viviana Artavia Salas, Heredia (CR)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 128 days.

(21) Appl. No.: 17/404,548

(22) Filed: Aug. 17, 2021

(65) Prior Publication Data

US 2022/0061848 A1 Mar. 3, 2022

Related U.S. Application Data

(60) Provisional application No. 63/073,189, filed on Sep. 1, 2020.

(51) Int. Cl.
*A61B 17/11* (2006.01)

(52) U.S. Cl.
CPC ... *A61B 17/1114* (2013.01); *A61B 2017/1103* (2013.01); *A61B 2017/1139* (2013.01)

(58) Field of Classification Search
CPC ................ A61B 17/068; A61B 17/122; A61B 2017/0417
See application file for complete search history.

(56) References Cited

U.S. PATENT DOCUMENTS 5,275,611 A 1/1994 Behl
5,282,813 A * 2/1994 Redha ............. A61B 17/32075 606/159

(Continued)

FOREIGN PATENT DOCUMENTS

EP 1550415 A2 7/2005
EP 1894514 A2 3/2008

(Continued)

OTHER PUBLICATIONS

Author Unknown, "Axios Stent and Electrocautery Enhanced Delivery System" retrieved Mar. 20, 2020—Boston Scientific URL: https://www.bostonscientific.com/content/gwc/en-us/products/stents-gastrointestinal/axios-stent-and-electrocautery-enhanced-delivery-system.html.

(Continued)

*Primary Examiner* — Kathleen S Holwerda
*Assistant Examiner* — Serenity A Miller
(74) *Attorney, Agent, or Firm* — Seager, Tufte & Wickhem, LLP

(57) ABSTRACT

A tissue-manipulating system including a tissue-manipulating device having a tissue grasper assembly with at least one grasper arm movably coupled to a shaft to move between a closed configuration and an open configuration. The at least one grasper arm may be pivotably coupled to the shaft, such as via a collar. A tissue-manipulating device controller is coupled to the tissue grasper assembly to move the at least one grasper arm between the closed and open configurations. The tissue grasper assembly is positionable to move a distal tissue wall closer to a proximal tissue wall. The tissue grasper assembly may be deployable (such as by separating from the shaft) to remain in place holding the distal tissue wall and proximal tissue wall in apposition.

20 Claims, 13 Drawing Sheets

(56) References Cited

U.S. PATENT DOCUMENTS

| | | | | |
|---|---|---|---|---|
| 8,357,193 | B2 | 1/2013 | Phan et al. | |
| 8,454,632 | B2 | 6/2013 | Binmoeller et al. | |
| 8,617,159 | B2 | 12/2013 | Roberto et al. | |
| 8,801,647 | B2 | 8/2014 | Melanson et al. | |
| 8,876,699 | B2 | 11/2014 | Sato et al. | |
| 11,389,185 | B2 | 7/2022 | Golden et al. | |
| 2005/0143763 | A1 | 6/2005 | Ortiz et al. | |
| 2006/0020275 | A1* | 1/2006 | Goldfarb ................ | A61B 17/08 606/151 |
| 2007/0010715 | A1 | 1/2007 | Sixto et al. | |
| 2010/0268029 | A1 | 10/2010 | Phan et al. | |
| 2014/0243586 | A1 | 8/2014 | Rohaninejad et al. | |
| 2016/0000433 | A1 | 1/2016 | Raybin et al. | |
| 2019/0261996 | A1 | 8/2019 | Goldfarb et al. | |
| 2019/0298401 | A1 | 10/2019 | Gupta et al. | |

FOREIGN PATENT DOCUMENTS

| | | | |
|---|---|---|---|
| JP | 52-32995 | U | 3/1977 |
| JP | S5232995 | U | 3/1977 |
| WO | 2007115117 | A1 | 10/2007 |

OTHER PUBLICATIONS

Author Unknown, "Axios Stent and Delivery System—Prescriptive Information"—Boston Scientific 2015.

International Search Report and Written Opinion for International Application No. PCT/US2021/046296 dated Nov. 19, 2021.

* cited by examiner

GRASPING DEVICES, SYSTEMS, AND METHODS FOR TISSUE APPROXIMATION AND APPOSITION

PRIORITY

The present application is a non-provisional of, and claims the benefit of priority under 35 U.S.C. § 119 to U.S. Provisional Application Ser. No. 63/073,189, filed Sep. 1, 2020, the disclosure of which is hereby incorporated herein by reference in its entirety for all purposes.

FIELD

The present disclosure relates generally to apparatus and methods for manipulating a tissue wall and/or approximating tissue walls and/or maintaining tissue walls in apposition.

BACKGROUND

Tissue approximation is useful in many medical procedures for a variety of purposes. A number of medical procedures require a tissue wall (e.g., a body lumen wall or the wall of an organ) to be moved to a desired position, such as relative to another tissue wall to form an anastomosis between adjacent body lumens or to repair a body tissue. Challenges occur when moving a lumen towards another lumen and to anchor the two in place.

Improved tools, devices, systems, and methods for manipulating and moving body organs, tissues, lumens, and the like would thus be welcome in the medical field.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

The present disclosure is directed to a tissue-manipulating device and system capable of manipulating, grappling, grasping, approximating, drawing, pulling, holding, etc., (such terms being used interchangeably herein without intent to limit) tissue walls. Optionally, the device and system may be used to hold the tissue together in apposition. It is desirable to provide improved protocols and access and tissue-grasping/tissue-grappling tools, devices, and systems for drawing tissues together, such as for forming an anastomosis or repairing tissue. It is further desirable to provide protocols, tools, devices, and systems facilitating quicker methods for forming anastomoses. It is further desirable to provide protocols, tools, devices, and systems for holding tissue in apposition (such as while also minimizing any risk of leakage between the tissues).

In various embodiments described or otherwise within the scope of the present disclosure, the present subject matter is directed to a tissue-manipulating device and system capable of manipulating, grappling, grasping, approximating, drawing, pulling, holding, etc., (such terms being used interchangeably herein without intent to limit) tissue walls. Optionally, the device and system may be used to hold the tissue together in apposition.

In one aspect, the present disclosure relates to a tissue manipulating device comprising a shaft; a tissue grasper assembly coupled to a distal end of the shaft; and a controller coupled to the tissue grasper assembly. In some embodiments, the tissue grasper assembly comprises one or more grasper arms movable between a closed configuration extending along the shaft and an open configuration extending away from the shaft. In some embodiments, the controller is configured to move the grasper arms between the closed configuration and the open configuration. In some embodiments, at least one of the grasper arms has a grasper surface shaped and configured to engage a body tissue such that when the at least one grasper arm is in an open configuration and the grasper surface contacts a body tissue and the tissue-manipulating device is moved proximally, the tissue-manipulating device moves the body tissue proximally as well.

In some embodiments, the grasper arms are pivotably coupled to the shaft.

In some embodiments, the tissue grasper assembly is separable from the shaft and the controller to remain deployed grasping body tissue.

In some embodiments, the tissue grasper assembly comprises a locking feature engageable to hold the at least one grasper arm in one of the closed configuration or the open configuration when the tissue grasper assembly is separated from the shaft and the controller.

In some embodiments, the tissue-manipulating device further comprises a controller coupling coupled between the grasper arms and the controller, and movable upon actuation of the controller to move the at least one grasper arm between the closed configuration and the open configuration.

In some embodiments, the tissue grasper assembly further comprises a collar coupled to the shaft, the grasper arms being coupled to the shaft via the collar.

In some embodiments, the collar and the controller coupling comprise interengaging locking features configured to hold the controller coupling in place to hold the at least one grasper arm in the closed configuration.

In some embodiments, the controller coupling comprises a plurality of linkage arms coupled to move the grasper arms between the closed configuration and the open configuration.

In some embodiments, the controller coupling comprising at least two controller elements coupled respective first and second grasper arms to independently control the first and second grasper arms.

In accordance with other or additional aspects, the present disclosure relates to a tissue grasper assembly comprising a collar configured for coupling with a distal end of a shaft; one or more grasper arms pivotably coupled with the collar; and a controller coupling coupled to at least one of the grasper arms and movable to move the at least one grasper arm between a closed configuration extending along the collar and an open configuration extending away from the collar. In some embodiments, each grasping arm has a grasper surface shaped and configured to engage a body tissue. In some embodiments, when in a closed configuration, the grasper surface is configured to hold a body tissue between the grasper surface and the collar.

In some embodiments, the collar and the grasper arms having matching outer surface contours to provide a low profile contour to the tissue grasper assembly when the grasper arms are in a closed configuration.

In some embodiments, each of the grasper arms has a coupling end coupled to the collar and a free end extending away from the collar, the free end of at least one of the grasper arms including a grasping feature facilitating engagement of the free end of the at least one grasper arm with a body tissue.

In some embodiments, the tissue grasper further comprises a sharpened element extending distally from the tissue grasper assembly and configured for puncturing a body tissue wall.

In some embodiments, the controller coupling comprises a plurality of linkage arms coupled to move the grasper arms between the closed configuration and the open configuration.

In accordance with other or additional aspects, the present disclosure relates to a method of manipulating tissue with a tissue-manipulating device, the method comprising extending a tissue-manipulating device through a proximal tissue wall and a distal tissue wall to move a distal end of the tissue-manipulating device distal to the distal tissue wall, actuating a tissue-manipulating device controller to pivot the at least one grasper arm relative to the tissue-manipulating device controller and into an open configuration engaging a distal side of the distal tissue wall; and moving the tissue-manipulating device proximally to move the distal tissue wall in apposition to the proximal tissue wall. In some embodiments, the tissue-manipulating device comprises a shaft and a tissue grasper assembly. In some embodiments, the tissue grasper assembly comprises at least one movable grasper arm pivotably coupled to the shaft and in a closed configuration extending along the shaft when the tissue-manipulating device is extended through the proximal tissue wall and the distal tissue wall.

In some embodiments, the distal end of the tissue grasper assembly comprises a sharpened element, and the method further comprises extending the tissue-manipulating device through a proximal tissue wall and a distal tissue wall and puncturing the proximal tissue wall and the distal tissue wall with the sharpened element.

In some embodiments, the method further comprises separating the tissue grasper assembly from the shaft to deploy the tissue grasper assembly holding the proximal tissue wall and the distal tissue wall in apposition.

In some embodiments, the tissue grasper assembly comprises a collar coupling the tissue grasper assembly to the shaft and a controller coupling coupling the tissue-manipulating device controller with the at least one grasper arm, and the method further comprising locking the controller coupling with the collar to hold the tissue grasper assembly in a configuration grasping the proximal tissue wall and the distal tissue wall in apposition.

In some embodiments, the method further comprises actuating the tissue-manipulating device controller to pivot the at least one grasper arm into the closed configuration with the at least one grasper arm engaging the distal tissue wall to hold the distal tissue wall in place relative to the tissue grasper assembly when manipulating the tissue-manipulating device to move the distal tissue or to hold the distal tissue wall in place relative to the proximal tissue wall.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
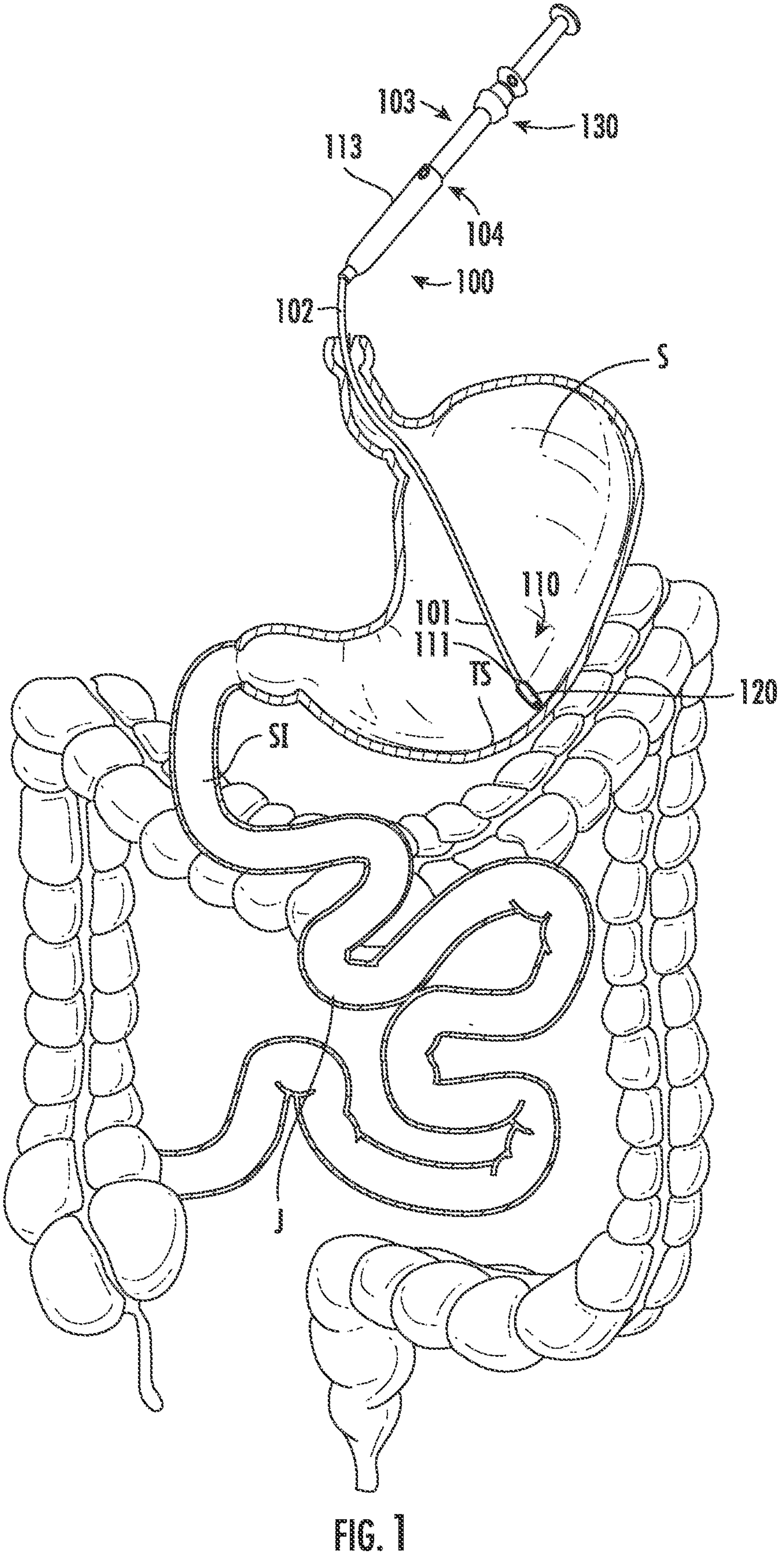
FIG. 1 is a schematic illustration of a human gastrointestinal system as an example environment in which embodiments of the present disclosure may be applied or used or deployed.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, “proximal” refers to the direction or location closest to the user (medical professional or clinician or technician or operator or physician, etc., such terms being used interchangeably without intent to limit or otherwise), etc., such as when using a device (e.g., introducing the device into a patient, or during implantation, positioning, or delivery), and “distal” refers to the direction or location furthest from the user, such as when using the device (e.g., introducing the device into a patient, or during implantation, positioning, or delivery). “Longitudinal” means extending along the longer or larger dimension of an element. “Central” means at least generally bisecting a center point, and a “central axis” means, with respect to an opening, a line that at least generally bisects a center point of the opening, extending longitudinally along the length of the opening when the opening comprises, for example, a tubular element, a channel, or a bore.

As will now be described with reference to the drawings, devices and systems and methods are disclosed herein for manipulating a tissue wall and/or approximating tissue walls and/or maintaining tissue walls in apposition at a treatment site. The medical devices, instruments, tools, etc. of the present disclosure are not limited, and may include a variety of medical devices for accessing body passageways, including, for example, duodenoscopes, catheters, ureteroscopes, bronchoscopes, colonoscopes, arthroscopes, cystoscopes, hysteroscopes, and the like. It should be appreciated that reference will be made herein to manipulating and/or other terms, such as grappling, grasping, approximating, drawing, pulling, holding, etc., such terms being used interchangeably herein without intent to limit. Tissue wall, such as, without limitation, organ or lumen walls, may be drawn closer together or to another tissue wall, such as to hold the tissue walls in apposition, such as to form an anastomosis. For instance, the device and system may engage and pull a portion of a small intestine toward a stomach wall, such as by puncturing through the walls of the small intestine and stomach, and hold the lumens/tissues together. Such methods and apparatus can also be used for access to and from portions of the urinary tract, such as the urinary bladder and ureter, the pulmonary tract, such as the trachea and bronchi, and the biliary tract, such as the bile duct and gallbladder, and vascular applications, as well. Alternatively, separated ends of tissue wall may be drawn together to close a defect therebetween. It will be appreciated that the present disclosure should not be interpreted as being limited to such procedures or end results. Moreover, although reference is made to a treatment site, such reference is merely for the sake of convenience and not intended to limit the scope of the disclosure.

In accordance with various principles of the present disclosure, the distal end of a tissue-manipulating device has an elongate member (e.g., catheter, shaft, etc.), referenced herein as a shaft for the sake of simplicity and without intent to limit, through (or along) which one or more grasper arms may be extended. In some embodiments the shaft is in the form of a collar. In some embodiments, the shaft includes a collar formed separately from the shaft and coupled thereto, and optionally removable from the shaft for deployment of the tissue grasper assembly (including the grasper arms) of the tissue-manipulating device. The grasper arms are movable between a closed configuration within the shaft (and generally extending within a lumen defined within the shaft and along the longitudinal or axial extent of the lumen and shaft), and an open configuration in which the grasper arms expand or extend away from the shaft, such as to engage tissue wall. In some embodiments, the grasper arms are resiliently biased, such as to be held in an open configuration capable of engaging tissue. In some embodiments, the grasper arms are resiliently biased to expand or otherwise to extend into an open configuration upon release or deployment from the shaft. In other embodiments, another element of the tissue manipulating device may hold the resiliently biased grasper arms in an open configuration.

A controller may extend along (e.g., through) the flexible elongate member from a proximal end of the flexible elongate member to the distal end of the flexible elongate member where the distal end of the controller is coupled with or engages at least one grasper arm to control movement of the grasper arm as desired or indicated by the procedure with which the tissue-manipulating device is used. The proximal end of the controller may be engaged with or coupled to or otherwise associated with a control handle facilitating actuation of the controller. Any of a variety of control handles known or heretofore known in the art may be used to manipulate the controller, such as via the proximal end thereof, the particular details of the configuration not limiting the scope of the present disclosure.

The distal end of the controller may be configured in any of a variety of manners to effect movement of the grasper arms. Various distal configurations of the controller, typically engaging or otherwise coupled to or associated with (such terms being used interchangeably herein without intent to limit) the grasper arms, may be interchangeable with various proximal configurations of the controller via which the controller is actuated to manipulate or control or actuate (such terms used interchangeably herein without intent to limit) the grasper arms. In some embodiments, the grasper arms are coupled to the tissue-manipulating device via linkage arms. In some embodiments, the controller may be distally advanced or proximally retracted to manipulate the relative positions of the grasper arms to cause the grasper arms to move between the closed configuration and the open configuration.

In accordance with some embodiments disclosed herein, the grasper arms may be coupled to a tissue grasper assembly configured to be releasable from the tissue-manipulating device shaft for deployment. The shaft may then be withdrawn, with the tissue grasper assembly maintaining the approximated tissues in apposition to each other.

In accordance with some embodiments disclosed herein, the distal end of the tissue-manipulating device may be configured to facilitate passage thereof through tissue walls to be manipulated. In some embodiments, the distal end of the tissue-manipulating device is provided with a sharp end, such as a needle or other sharpened element, capable of puncturing tissue walls. In some embodiments, the sharp end may be associated with the shaft and/or grasper arms.

Various features may be provided to facilitate grasping, grappling, moving, etc. (such terms being used interchangeably herein without intent to limit) the tissue. In accordance with some embodiments described herein, at least one of the grasper arms may be shaped and configured to enhanced engagement and/or grasping of tissue. In some embodiments, at least one of the free ends (e.g., distal ends) of at least one of the grasper arms is shaped and configured to enhanced engagement and/or grasping of tissue, such as by latching onto the tissue. In some embodiments, one or more tissue grasping features, such as hooks, are provided along one or both of the grasper arms between the attached end (the end coupled to the rest of the tissue-manipulating device, such as a distal end of the grasper arms) and the free end of the grasper arm.

Various embodiments of tissue-manipulating devices, systems, and methods will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

Turning now to the drawings, a tissue-manipulating system 100 formed in accordance with principles of the present disclosure is illustrated in a schematic representations of a gastrointestinal system, such as to create an anastomosis between a stomach S and a portion of the small intestine SI, such as the jejunum J. It will be appreciated that the gastrointestinal system is simply one of a number of anatomical sites in which a tissue-manipulating system 100 formed in accordance with principles of the present disclosure may be used, the particular anatomical site not affecting the scope of the present disclosure or limiting the disclosed tissue-manipulating system 100. The tissue-manipulating system 100 may include a delivery device, such as a flexible elongate member 102, such as an endoscope, cannula, delivery shaft, etc., (the term flexible elongate member being used herein to refer to the delivery device in general for the sake of convenience and without intent to limit) having a working channel therethrough via which a tissue-manipulating device 110 is guided to a treatment site TS. The tissue-manipulating device 110 includes a tissue grasper assembly 120 at a tissue-manipulating device distal end 111. A tissue-manipulating device controller 130 (shown schematically) extends from the tissue grasper assembly 120 to a proximal end 103 of the tissue-manipulating system 100 for access and manipulation by the user (e.g., medical professionals, such as physicians, technicians, endoscopists, etc., or automated system or otherwise) to control the tissue grasper assembly 120. The tissue-manipulating device 110 may be arranged with respect to the tissue-manipulating system 100 such that the tissue grasper assembly 120 extends from a distal end 101 of the tissue-manipulating system 100, and such that a proximal end 133 of the tissue-manipulating device controller 130 is positioned at or along a proximal end 103 of the tissue-manipulating system 100. A control handle 104 may be provided at a proximal end 103 the tissue-manipulating system 100 and may be associated with the tissue-manipulating device controller 130 and/or a controller of the flexible elongate member 102 (any controller known or heretofore known in the art and not illustrated as not necessary for a complete understanding of the tissue-manipulating device 110).

Figure 2:
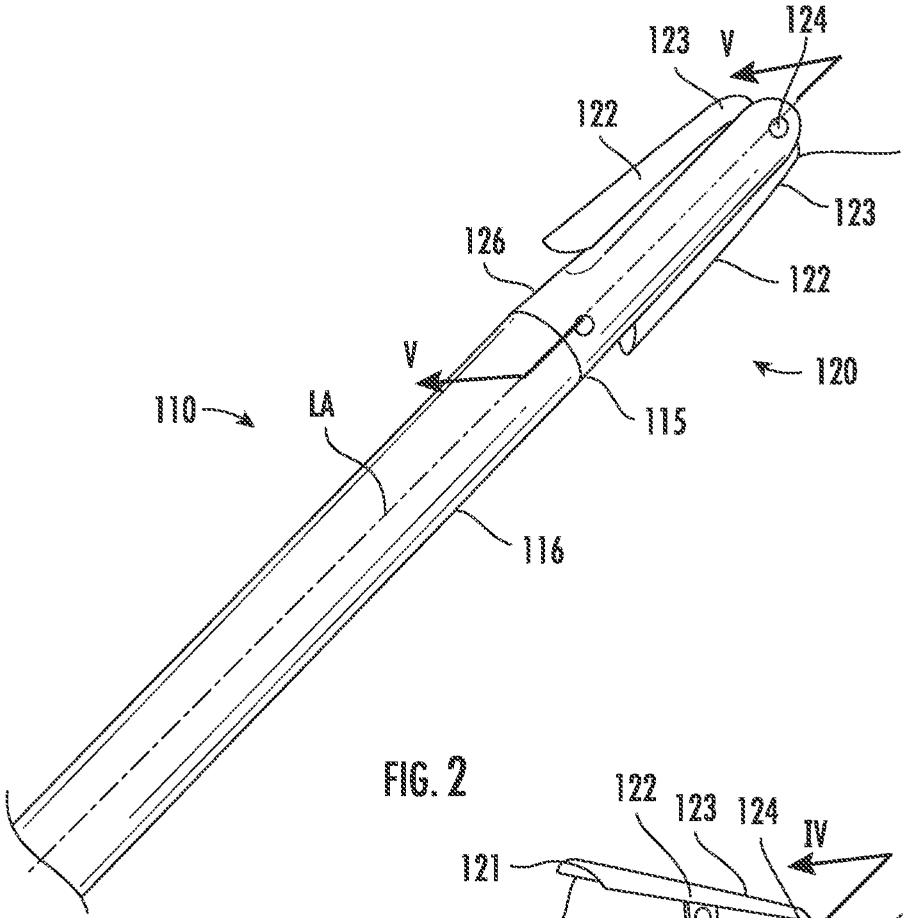
FIG. 2 is a proximal side perspective view of a tissue-manipulating device formed in accordance with principles of the present disclosure and shown in a closed configuration for delivery to a treatment site.

The tissue-manipulating device 110 is configured to be delivered through the flexible elongate member 102 to a treatment site TS in accordance with techniques for advancing devices or systems through a patient's anatomy to a treatment site TS known or heretofore known to medical professionals. The distal end 111 of the tissue-manipulating device 110 may have profile configured to readily pass through an opening through a tissue wall, such as illustrated in FIG. 2. For instance, the distal end 111 of the tissue-manipulating device 110 may be configured in a closed position with substantially blunt surfaces so as to readily pass through aperture or passage designated for (e.g., created for passage of or created by, as discussed in further detail below) the tissue-manipulating device 110 without creating any unwanted damage (e.g., abrasions, lacerations, tears, etc.). In some embodiments, the tissue-manipulating device 110 has a shaft 116 with a distal end 115 to which the tissue grasper assembly 120 is coupled, and the outer contour (e.g., the cross-sectional shape) of the sides of the tissue grasper assembly 120 (extending longitudinally/axially) substantially matches the outer contour (e.g., cross-sectional shape) of the sides shaft 116 (extending longitudinally/axially). For instance, if the shaft 116 has substantially circular cross-section, then the tissue grasper assembly 120 may have an outer surface that is convex about a longitudinal axis LA of the shaft 116.

Figure 3:
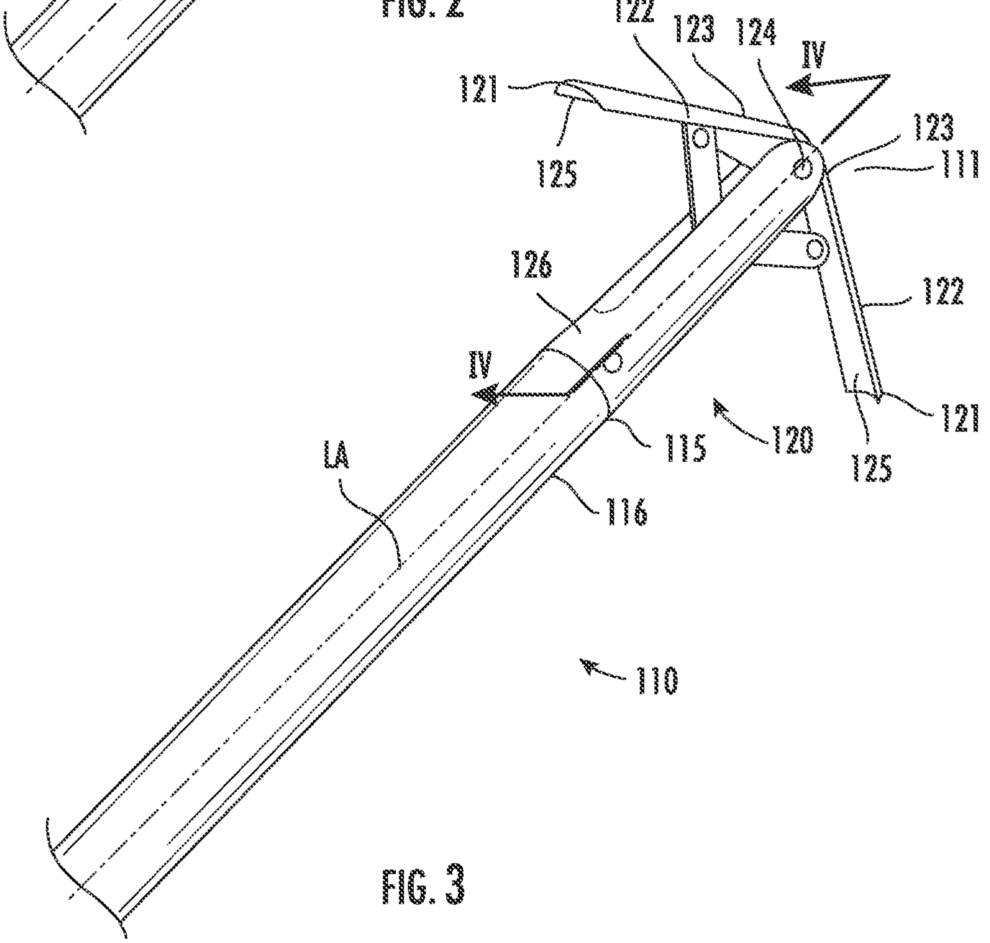
FIG. 3 is a proximal side perspective view of a tissue-manipulating device formed in accordance with principles of the present disclosure and shown in an open configuration for manipulating tissue.

In accordance with one aspect of disclosure, the tissue grasper assembly 120 includes one or more grasper arms 122 movably coupled to the shaft 116. In some embodiments, the grasper arms 122 are pivotably coupled to the shaft 116 about a pivot axis PA. The grasper arms 122 are movable or pivotable from the closed configuration of FIG. 2 to an open configuration, such as illustrated in FIG. 3, in which the grasper arms 122 are positioned away from or spaced apart from the shaft 116. In the open configuration, the grasper arm 122 extends away from the shaft 116 with a free end 121 (as used herein, a "free end" of an element is a terminal end at which such element does not extend beyond) of the grasper arm 122 spaced away from the shaft 116 and/or the grasper arm 122 itself is shaped and configured to present a grasper surface 125 shaped and configured and having sufficient gripper arm surface area to engage and manipulate tissue as desired. One or more of the grasper arms 122 are coupled to the shaft 116 via a grasper arm coupling 124, such as a pivot or other structure permitting relative movement (e.g., pivoting or rotating) of the grasper arm 122 relative to the shaft 116. In some embodiments, the tissue grasper assembly 120 includes a collar 126 fitted on the distal end 115 of the shaft 116, with the grasper arms 122 coupled to the shaft 116 via the collar 126. In some embodiments, the grasper arm coupling 124 is provided at a coupling end 123 of the grasper arm 122 spaced apart from the free end 121 of the grasper arm 122. In some embodiments, the grasper arm coupling end 123 is formed at a free end of the grasper arm 122 opposite the free end 121 of the grasper arm 122. It will be appreciated that although the grasper arms 122 are illustrated as being coupled with free end 121 extending proximally, and coupling ends 123 distal to the free end 121, other configurations and orientations are within the scope of the present disclosure.

The tissue-manipulating device controller 130 is coupled to the grasper arms 122 and extends proximally, such as to the proximal end 113 of the tissue-manipulating device 110 and/or the proximal end 103 of the tissue-manipulating system 100, for access by a user to actuate the tissue-manipulating device controller 130 to operate the grasper arms 122 to move as desired relative to the shaft 116. In some embodiments, the tissue-manipulating device controller 130 is moved distally or proximally to actuate the grasper arms 122. However, other movements or control of the tissue-manipulating device controller 130 are within the scope of the present disclosure, the particular movements not being critical to the broad principles of the disclosure.

The tissue-manipulating device controller 130 may be coupled to the grasper arms 122 with a coupling known or heretofore in the art capable of transmitting the desired control movements or actions from the tissue-manipulating device controller 130 to the grasper arms 122. In some embodiments, such as illustrated in FIGS. 4 and 5, the tissue-manipulating device controller 130 may include a controller element 132, such as a wire, with a fitment 134 at a distal end 131 thereof configured to be coupled to the tissue grasper assembly 120 via a controller coupling 140 to impart desired movements to the controller coupling 140 to actuate the grasper arms 122.

Figure 4:
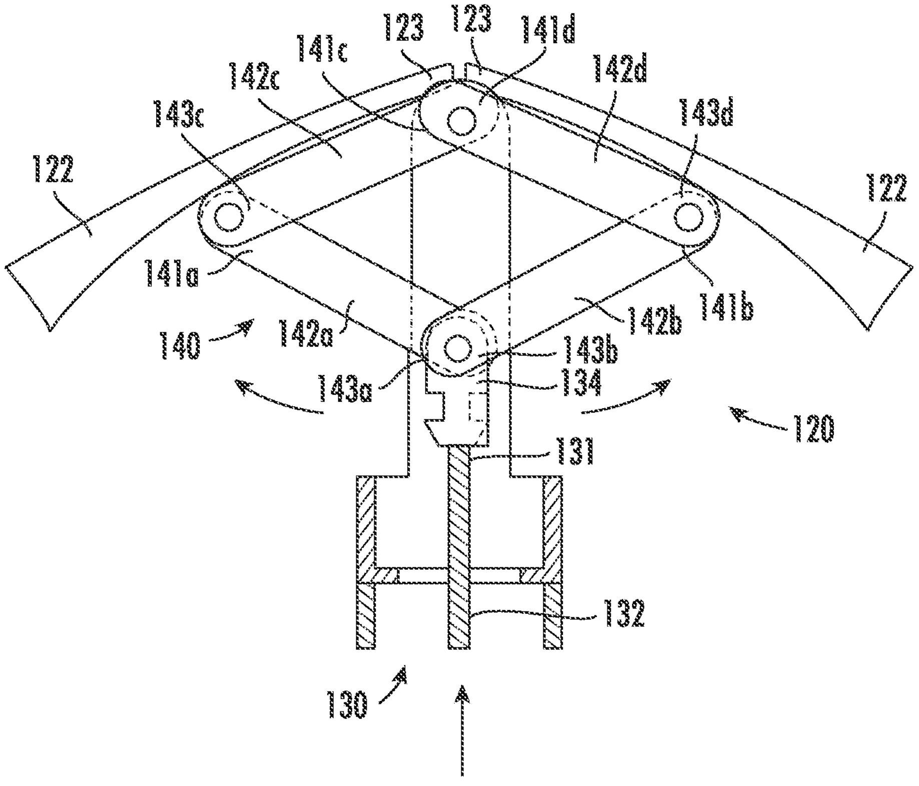
FIG. 4 is cross-sectional view along line IV-IV in FIG. 2, showing an example of a coupling between the grasper arms and controller of a tissue-manipulating device formed in accordance with principles of the present disclosure, with the grasper arms and coupling in an open configuration.
Figure 5:
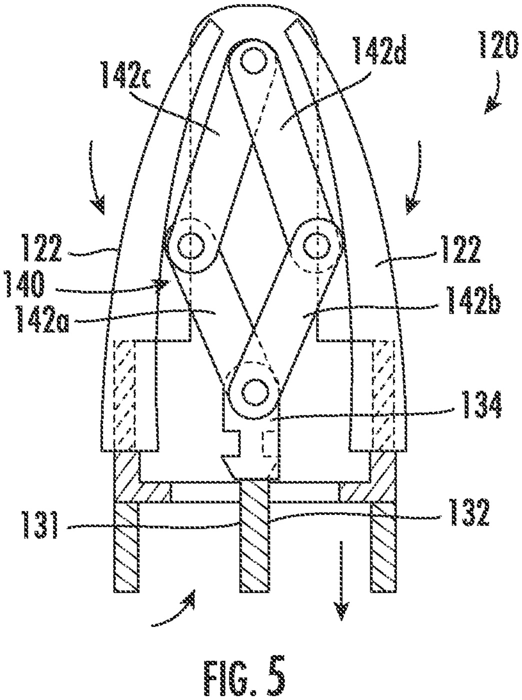
FIG. 5 is cross-sectional view along line V-V in FIG. 3, showing an example of a coupling between the grasper arms and controller of a tissue-manipulating device formed in accordance with principles of the present disclosure, with the grasper arms and coupling in a closed configuration.
Figure 6:
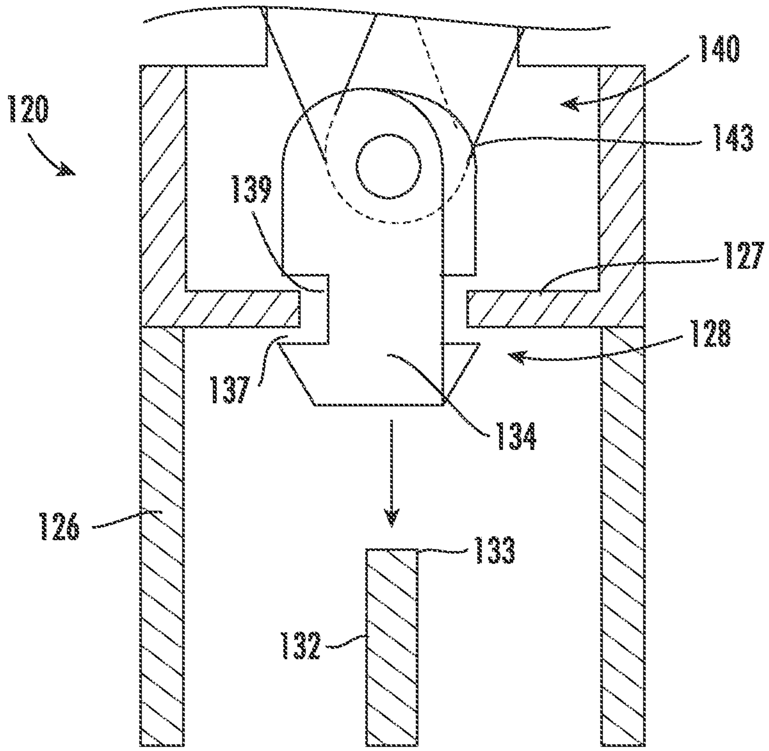
FIG. 6 is an embodiment of a grasping section according to the present disclosure.

In one embodiment, illustrated in FIGS. 4 and 5, the controller coupling 140 is in the form of linkage arms 142*a*, 142*b*, 142*c*, 142*d*. The controller element 132 of the tissue-manipulating device controller 130 may (such as via the fitment 134 at the distal end 131 of the controller element 132) be coupled with the controller coupling 140, such as via the proximal ends 143*a*, 143*b* of proximal linkage arms 142*a*, 142*b* of the controller coupling 140, such as via a pivotable or rotatable coupling (e.g., a pivot). The distal ends 141*a*, 141*b* of the proximal linkage arms 142*a*, 142*b* may be movably (e.g., pivotably or rotatably) to proximal ends 143*c*, 143*d* of the distal linkage arms 142*c*, 142*d*. The distal ends 141*c*, 141*d* of the distal linkage arms 142*c*, 142*d* may be movably (e.g., pivotably or rotatably) to the coupling end 123 of the grasper arms 122, such as via the grasper arm coupling 124. As may be appreciated with reference to the closed position illustrated in FIG. 4 and the open position illustrated in FIG. 5, distal movement of the tissue-manipulating device controller 130 actuates the controller coupling 140 to move from the configuration illustrated in FIG. 4 to the configuration illustrated in FIG. 5. As may be appreciated, the linkage arms 142*a*, 142*b*, 142*c*, 142*d* move from a collapsed configuration (when the tissue grasper assembly 120 is in the closed configuration of FIG. 4) to an expanded configuration (when the tissue grasper assembly 120 is in the open configuration of FIG. 5), and in so expanding, the linkage arms 142*a*, 142*b*, 142*c*, 142*d* move (e.g., by contacting) the grasper arms 122 to move the grasper arms 122 away from the closed configuration (adjacent or lying against or along the shaft 116) to the open configuration spaced apart and/or extending away from the shaft 116. In some embodiments, as illustrated in FIG. 6 and as will be described in further detail below, the tissue grasper assembly 120 may be left in place and the tissue-manipulating device controller 130 separated therefrom. It will be appreciated that other configurations of a tissue-manipulating device controller and a controller coupling are within the scope and spirit of the present disclosure, operation and movement of the grasper arms not being limited by a particular configuration of controller or controller coupling.

Figure 7A:
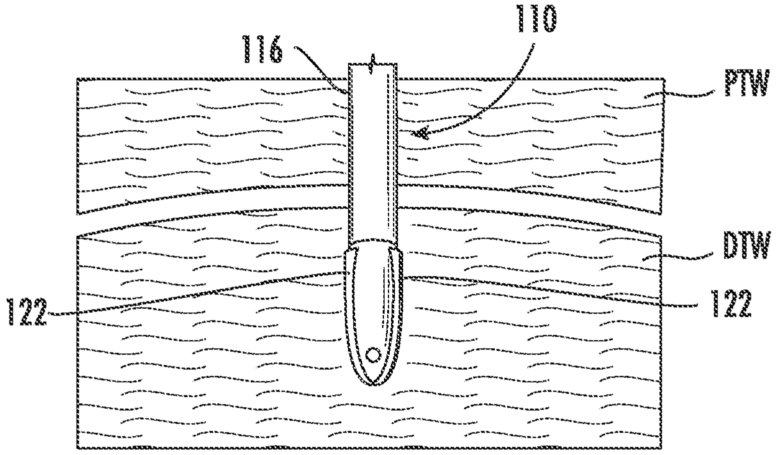
FIGS. 7A-7D illustrate sequential positions of a tissue-manipulating device formed in accordance with principles of the present disclosure with respect to tissues to be moved into apposition.
Figure 7B:
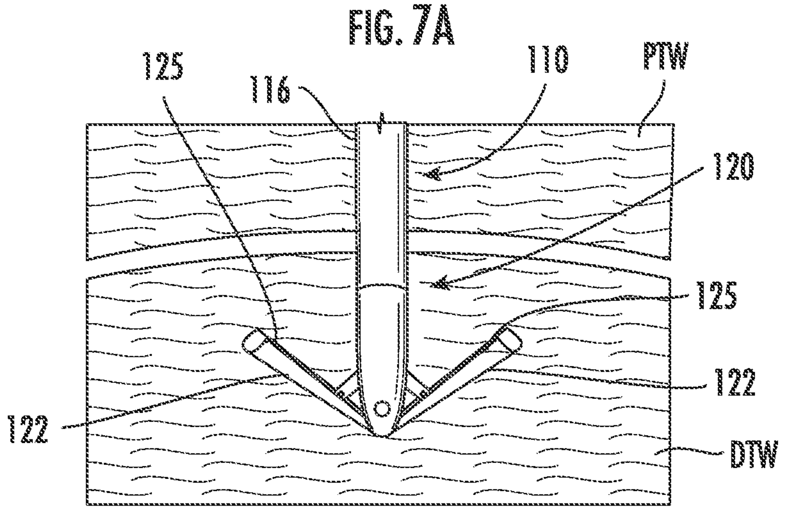
Figure 7C:
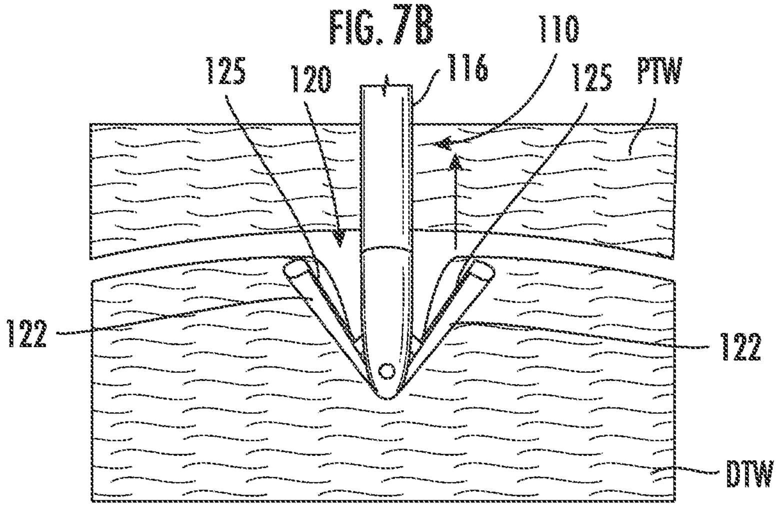
Figure 7D:
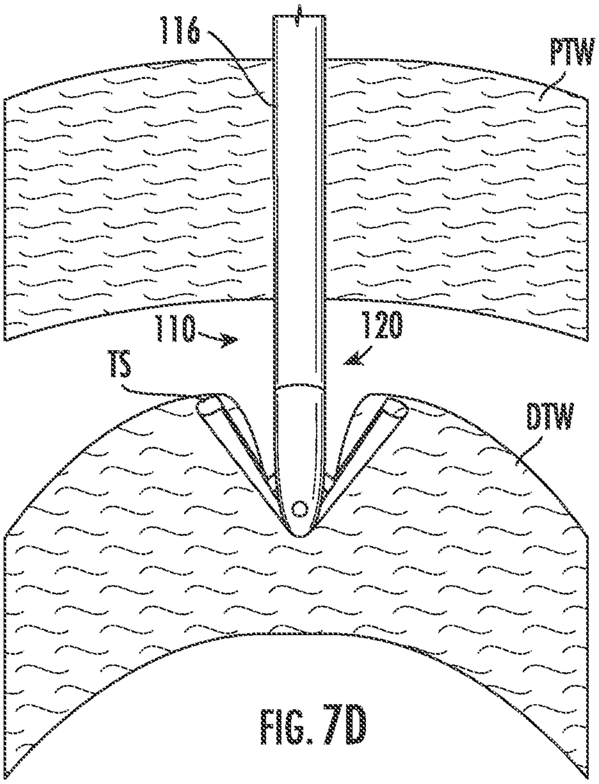

Examples of manipulations and movements of a tissue-manipulating device 110 formed in accordance with principles of the present disclosure, in use in accordance with some aspects of the present disclosure, are illustrated in FIGS. 8A-8D. As illustrated in FIG. 7A, the tissue-manipulating device 110 has already been advanced distally through a distal end of a delivery device (such as a flexible elongate member 102, if used), and through a proximal body cavity or lumen and through a proximal tissue wall PTW (e.g., an organ wall, such as a stomach wall, or a lumen wall distal to the proximal body cavity or lumen), and is shown being advanced through a distal tissue wall DTW and into a distal body cavity or lumen. In FIG. 7B, the tissue grasper assembly 120 is shown moving or having been moved into an open configuration (such as by operation of the tissue-manipulating device controller 130, not shown in this illustration). The tissue grasper assembly 120 is then moved proximally, as illustrated in FIG. 7C, to engage the distal tissue wall DTW. Optionally (as illustrated in FIG. 7C), the grasper arms 122 of the tissue grasper assembly 120 may be moved to a closed or partially closed configuration, bringing the grasper surface 125 (which faces the shaft 116 when the grasper arms 122 are in a closed configuration) of the grasper arms 122 closer to the shaft 116 to hold the distal tissue wall DTW between the grasper surface 125 and the shaft 116. However, the grasper arms 122 may remain in an open configuration if desired. As illustrated in FIG. 7D, the distal tissue wall DTW may then be manipulated as desired, such as proximally (for instance, a distal lumen may be moved proximally) towards and, optionally, in apposition with the proximal tissue wall PTW.

Figure 8A:
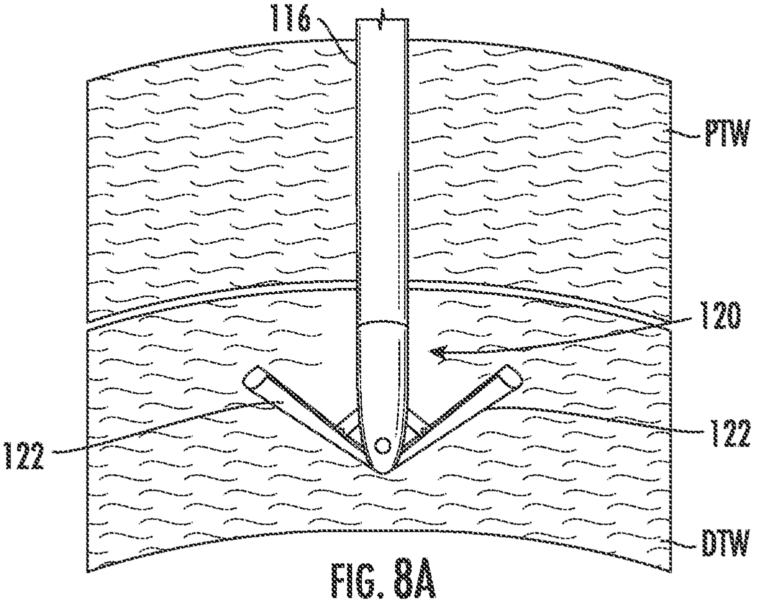
FIGS. 8A and 8B illustrate an example of further positions of a tissue-manipulating device after the position illustrated in FIG. 7D.
Figure 8B:
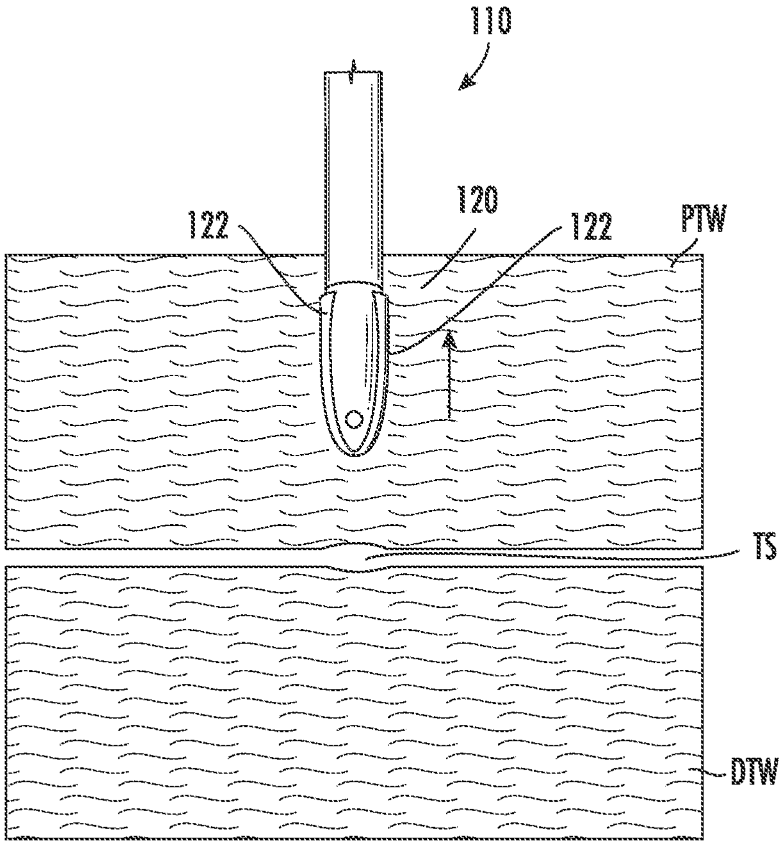

In accordance with one aspect of the disclosure, and as illustrated in FIGS. 8A and 8B, once the distal tissue wall DTW has been moved into apposition with the proximal tissue wall PTW, as illustrated in FIG. 8A, the tissue grasper assembly 120 may be moved out of engagement with the distal tissue wall DTW. The grasper arms 122 may be returned to a closed configuration, and moved proximally, such as out of the distal cavity, away from the treatment site TS, as illustrated in FIG. 8B such as for removal out of the body, etc. Further procedures may then be performed at the treatment site TS, as known or heretofore known in the medical field.

Figure 9:
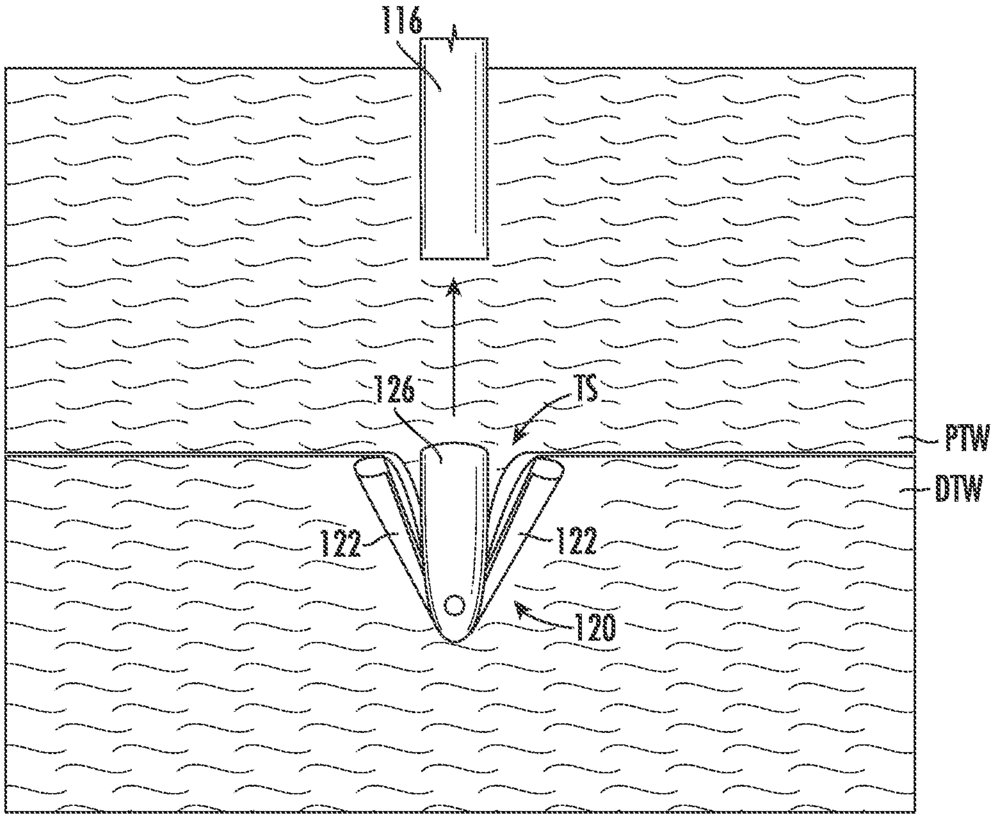
FIG. 9 illustrates an alternate example of a further position of a tissue-manipulating device after the position illustrated in FIG. 7D.

In accordance with one aspect of the disclosure, and as illustrated in FIG. 9, once the distal tissue wall DTW has been moved into apposition with the proximal tissue wall PTW, such as after the position illustrated in FIG. 7D, the shaft 116 may be uncoupled/detached from the tissue grasper assembly 120 The tissue grasper assembly 120 is thereby left in place, holding the proximal tissue wall PTW and the distal tissue wall DTW together, such that further procedures may be performed, or to reinforce holding together of tissue held together with a stent or otherwise in the area of the treatment site TS. In the example illustrated in FIG. 9, the grasper arms 122 are in a closed configuration holding the distal tissue wall DTW between the grasper arms 122 and the collar 126 of the tissue grasper assembly 120. However, alternate configurations allowing the grasper arms 122 to remain in an open configuration against the distal tissue wall DTW are within the scope and spirit of the present disclosure.

Any of a variety of locking features may be provided, in accordance with principles of the present disclosure, to hold the grasper arms 122 in place (in a closed configuration, as illustrated in FIG. 9, or in an open, expanded configuration) once the shaft 116 has been decoupled therefrom. In one embodiment, as illustrated in FIG. 6 (referenced briefly above), the tissue grasper assembly 120 may include a locking feature 128 configured to engage or interengage the fitment 134 on the tissue-manipulating device controller 130 and/or the proximal end 143 of controller coupling 140 with the collar 126. The tissue-manipulating device controller 130 may be manipulated (e.g., moved proximally and/or rotated or otherwise moved with respect to the collar 126) to engage or to actuate the locking feature 128 to hold the tissue grasper assembly 120 in a closed configuration. In one embodiment, as illustrated in the examples of FIG. 6, the locking feature is in the form of an inwardly directed flange 127 on the collar 126 and a corresponding flange 137 on the fitment 134. The fitment flange 137 may be dimensioned to be slightly greater in width (e.g., diameter) than the width of the collar flange 127 and resiliently flexible so that once the fitment flange 137 extends through and past the collar flange 127, the fitment flange 137 is held in place proximal to the collar flange 127. In some embodiments, the fitment flange 137 is defined by a distally extending groove 139 around the perimeter of the fitment 134 so that proximal and distal movement of the fitment 134 and the controller coupling 140 is restrained by engagement of the collar flange 127 within the groove 139. It will be appreciated that other arrangements, such as to hold the grasper arms 122 in an open configuration, are within the scope of the present disclosure. Once the controller coupling 140 is held in the desired position to hold the grasper arms 122 in the desired configuration, the tissue-manipulating device controller 130 may be decoupled (e.g., broken away from) from the controller coupling 140 and the shaft 116 may be decoupled from the controller coupling 140, as illustrated, leaving the controller coupling 140 in place holding the distal tissue wall DTW and proximal tissue wall PTW in the desired relative positions (e.g., in apposition). Any of a variety of configurations and methods of decoupling such components known or heretofore known in the art may be used without impacting the scope of the present disclosure.

Figure 10:
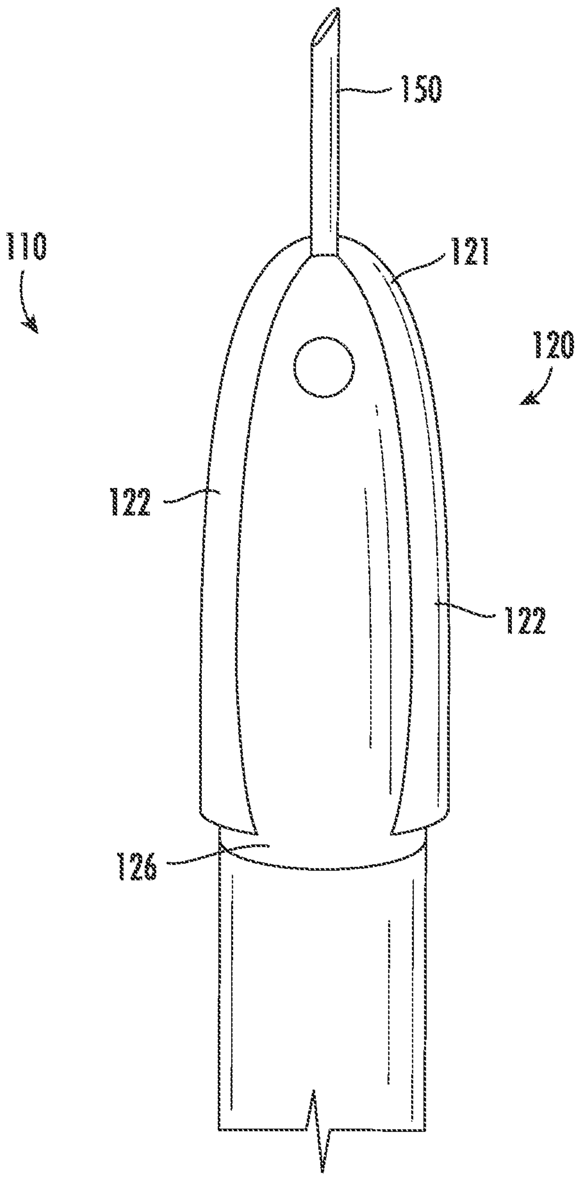
FIG. 10 is an elevational view of an embodiment of a distal end of a tissue-manipulating device formed to puncture tissue and with the grasper arms in a closed position.

Referring again to FIG. 7A, the opening through the tissue walls through which the tissue grasper assembly 120 is passed may be preformed in the tissue walls (such as by a separate cutting instrument) prior to insertion of the tissue grasper assembly 120 therethrough. In some embodiments, to facilitate the tissue manipulating procedure, such as by reducing operations and/or necessary instruments or devices, the tissue grasper assembly 120 may be configured to puncture the tissue walls and then pass therethrough. In some embodiments, the tissue grasper assembly 120 may be provided with a sharpened distal end extending distally from the tissue grasper assembly 120. In an embodiment, as illustrated in FIG. 10, a sharpened element 150, such as a needle, may be formed or positioned at the distal end 121 of the tissue grasper assembly 120 (e.g., on a distal end of the collar 126, if provided, or on at least one of the grasper arms 122). Distal advancement of the tissue grasper assembly 120 towards a tissue wall may engage the sharpened element 150 with the tissue wall, and further advancement causes the sharpened element 150 to puncture the tissue wall to allow the tissue grasper assembly 120 to pass therethrough. As will be appreciated, the grasper arms 122 preferably remain in a closed configuration, as illustrated, as the sharpened element 150 punctures the tissue wall. The tissue-manipulating device 110 may be further advanced to advance the sharpened element 150 at the distal end 151 of the tissue grasper assembly 120 towards another tissue wall to puncture the other tissue wall to allow the tissue grasper assembly 120 to pass therethrough as well. Further manipulation of the tissue-manipulating device 110, such as illustrated in any of FIGS. 7B, 7C, 7D, 8A, 8B, 9, may be performed.

Figure 11A:
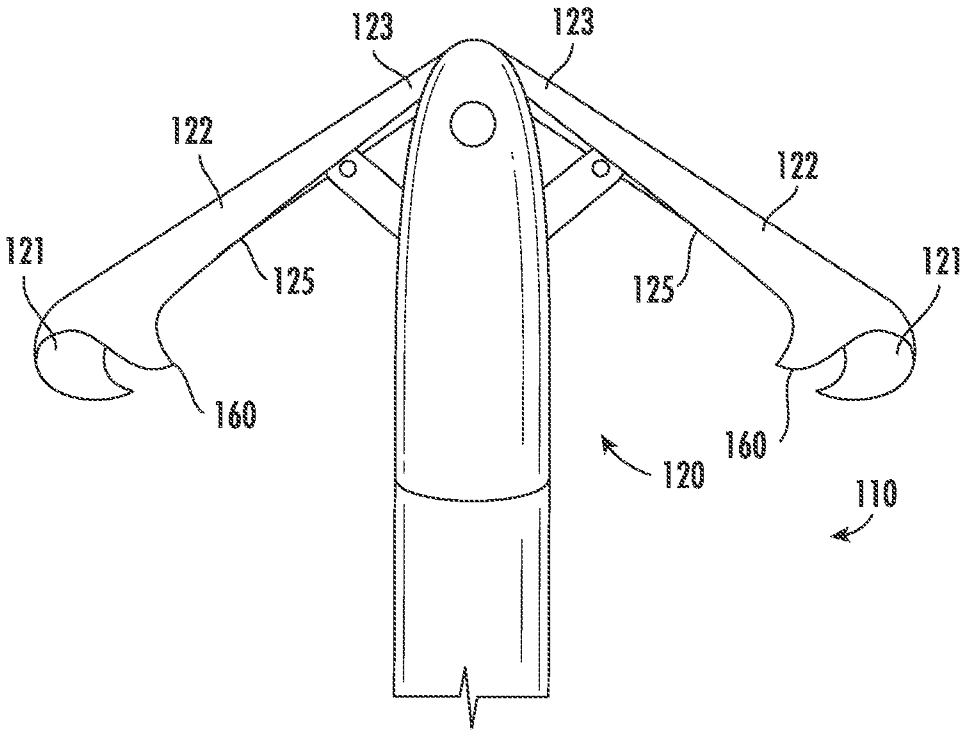
FIG. 11A is an elevational and partially perspective view of an embodiment of grasper arms of a tissue-manipulating device formed in accordance with principles of the present disclosure to enhance tissue grasping and in an open position.
Figure 11B:
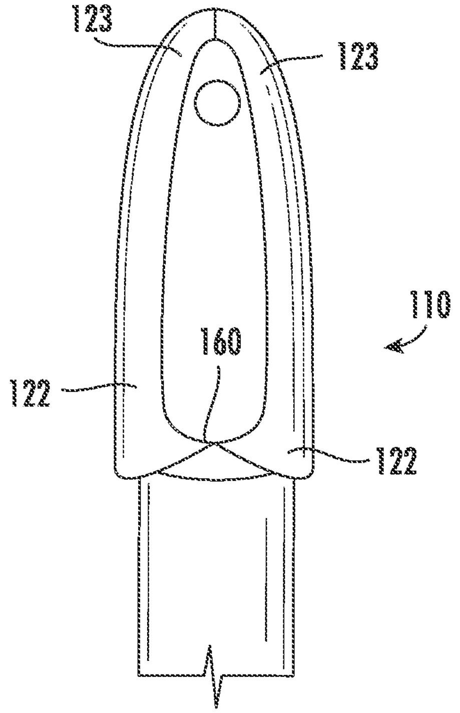
FIG. 11B is an elevational view of an embodiment of grasper arms of a tissue-manipulating device formed in accordance with principles of the present disclosure to enhance tissue grasping and in a closed position.

Referring again to FIG. 7C, in some embodiments it may be desirable to provide grasping features on the grasper arms 122 to facilitate grasping, grappling, moving, etc. the tissue. In one embodiment, as illustrated in FIGS. 11A and 11B, a free end 121 of one or more of the grasper arms 122 may be provided with a tissue grasping feature 160, such as a barb or hook or jaw or other tissue-engaging projection. Additionally or alternatively, one or more grasping features 160 may be provided along the grasper surface 125 between the free end 121 and the coupling end 123 of the grasper arm 122. The tissue grasping feature 160 is configured to enhance grasping of (e.g., latching onto) tissue so that grasper arms 122 do not inadvertently move with respect to the tissue wall being manipulated, or tissue walls held in place by a tissue grasper assembly 120 deployed and left in place for such function (e.g., as described above with reference to FIG. 9). In accordance with some aspects of the present disclosure, the grasping feature 160 may be used to facilitate use of the tissue grasper assembly 120 to repair defects, as will now be described.

Figure 12A:
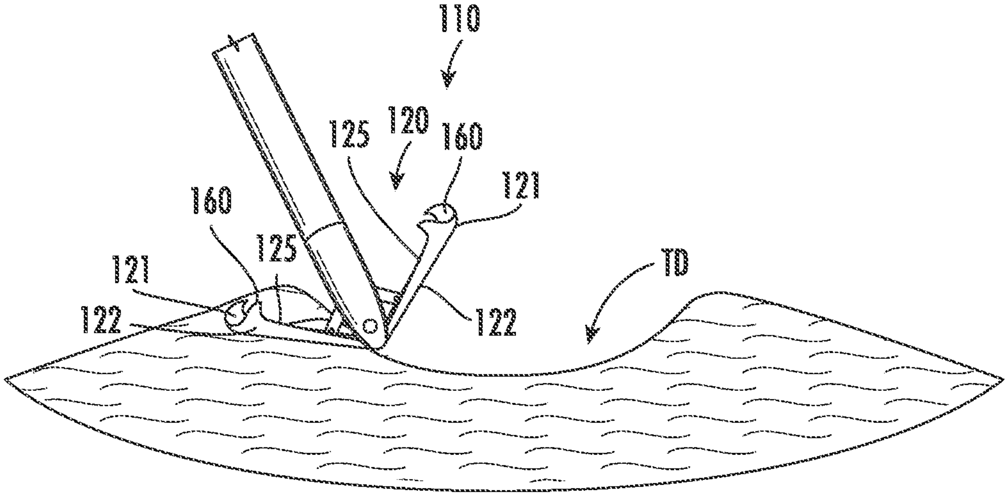
FIGS. 12A-12D illustrate sequential positions of a tissue-manipulating device, with grasper arms formed as in FIGS. 11A and 11B, with respect to a tissue defect to be repaired in accordance with principles of the present disclosure.
Figure 12B:
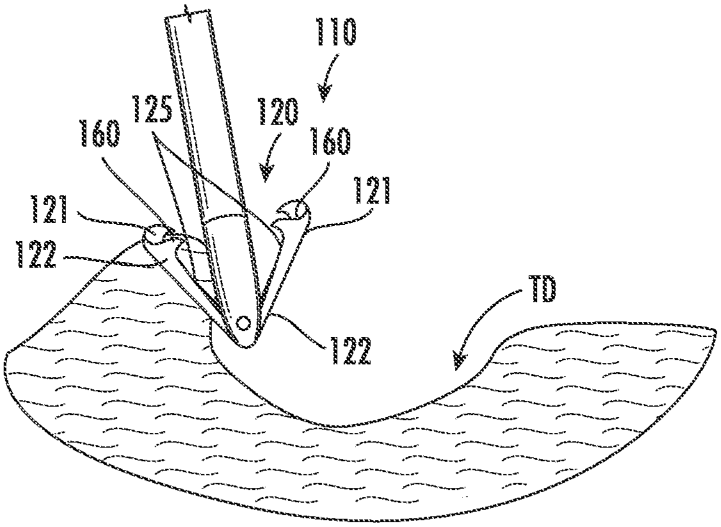
Figure 12C:
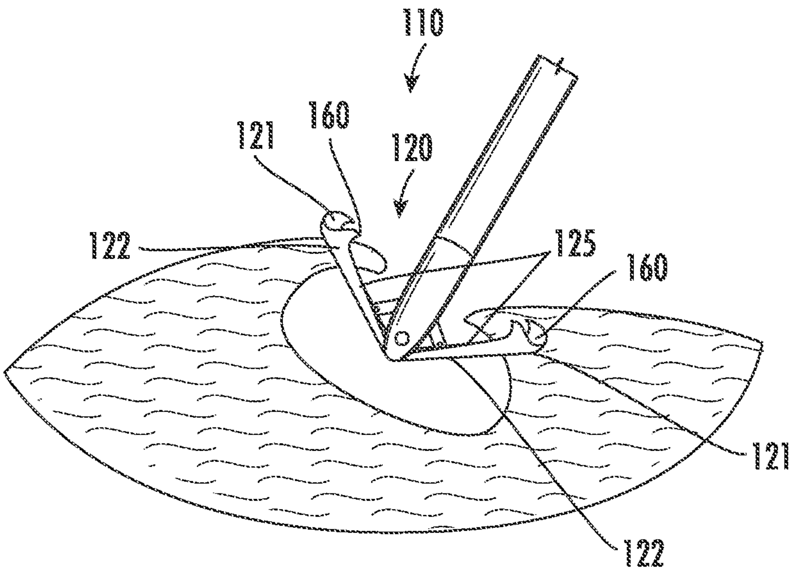
Figure 12D:
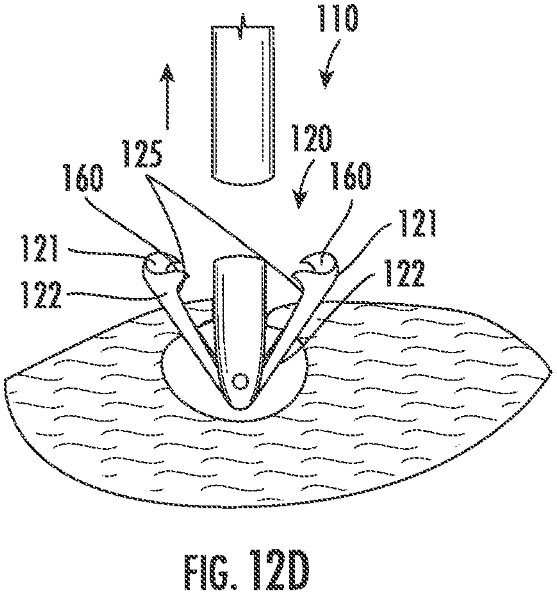

As may be appreciated, a tissue-manipulating device 110 in accordance with principles of the present disclosure may be used in a variety of procedures other than drawing and/or holding together tissue walls of different organs or lumens. For example, as illustrated in FIGS. 12A-12D, a tissue-manipulating device 110 may be used to repair a defect, such as by drawing together tissue walls at different sides or edges of the defect. As illustrated in FIG. 12A, a tissue grasper assembly 120 may be advanced to a tissue defect TD and one of the grasper arms 122 may be engaged with tissue wall along a side or edge of the tissue defect TD, such as by engaging a grasping feature 160 of the grasper arm 122 with the tissue. The grasper arm 122 is in an open configuration in the illustration of FIG. 12A to facilitate engagement of a portion of the grasper arm 122 (such as the distal end 121 of the grasper arm 122, a grasper surface 125 of the grasper arms 122, a grasping feature 160 of the grasper arm 122, etc.) with the tissue. The grasper arm 122 is then moved into a closed configuration, as illustrated in FIG. 12B, to maintain the relative positions and grasping of the tissue grasper assembly 120 and the grasped tissue region. The tissue grasper assembly 120, along with the grasped tissue, is then moved across the defect and another grasper arm 122 is extended to engage another region of the tissue wall along the tissue defect TD (such as tissue wall on another side of the tissue defect TD from the already-grasped tissue wall section), as illustrated in FIG. 12C. The grasping feature 160 of the grasper arm 122 engaging the initially-grasped tissue region facilitates maintaining the hold of the grasper arm 122 on the initially-grasped tissue region even if such grasper arm 122 is moved into an open configuration. The grasper arms 122, at least two of which are engaged with tissue surrounding the tissue defect TD, may then be moved to closed configurations, as illustrated in FIG. 12C, to effect defect closure. The tissue grasper assembly 120 may be left in place in the closed configuration, holding the tissue walls in apposition and decreasing the size of the tissue defect TD to allow for the defect to heal. As may be appreciated, the grasping feature 160 may facilitate the holding of the tissue grasper assembly 120 onto the tissue during the entire repair procedure.

To facilitate procedures, such as tissue repair, in which it may be desirable for one grasper arm 122 to be in a closed configuration while another grasper arm 122 is in an open configuration, independent operation of the grasper arms 122 may be desired such that each grasper arm 122 may be moved between open and closed configurations independently. It will be appreciated that independent operation of the grasper arms 122 may facilitate tissue repair without the aid of grasping features 160 on the grasper arms 122 as the initially grasped tissue region may be sufficiently or adequately grasped by the tissue grasper assembly 120 by closing the grasper arm 122 engaging such initially-grasped tissue region.

Figure 13:
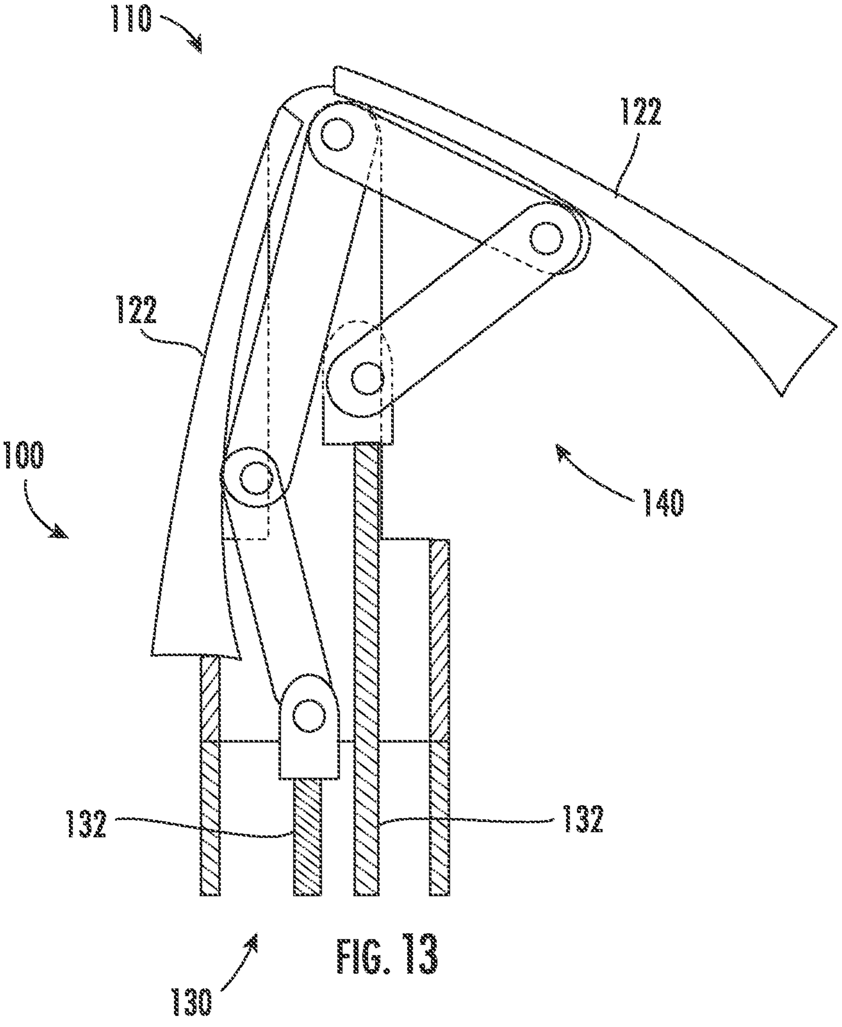
FIG. 13 a cross-sectional an embodiment of a controller in accordance with principles of the present disclosure.

An example of a tissue-manipulating device controller 130 and controller coupling 140 allowing for independent movement of grasper arms 122 is illustrated in FIG. 13. As shown, the tissue-manipulating device controller 130 includes more than one controller element 132, each controller element 132 engaging a different grasper arm 122. Operation of the controller elements 132 and controller coupling 140 may be similar to that of the embodiments of FIGS. 4 and 5, and reference is made to description thereof. It will be appreciated that other configurations are within the scope of the present disclosure.

In view of the above descriptions, it will be appreciated that the devices, systems, and methods disclosed herein can be used to form one or more anastomoses, and can be used with basic endoscopic tools, catheters, laparoscopes, general surgery tools, etc. For example, a catheter-based stent delivery device can be used with an endoscope to form one anastomosis, for example between two portions of the intestines. An endoscopic-based device could be used to form an anastomosis between the fundal pouch and a portion of the intestines, such as the jejunum. A combination of a laparoscopic-based device and a catheter-device as described herein could also be used to form a single anastomosis.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure. Reference signs in the claims are provided merely as a clarifying example and shall not be construed as limiting the scope of the claims in any way.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "the", "first", "second", etc., do not preclude a plurality. Reference signs in the claims are provided merely as a clarifying example and shall not be construed as limiting the scope of the claims in any way.

What is claimed is:

1. A tissue manipulating device comprising:

a shaft;

a collar coupled to a distal end of said shaft;

a tissue grasper assembly coupled to a distal end of said collar and comprising one or more grasper arms movable between a closed configuration extending along said collar and an open configuration extending away from said collar; and a controller having a distal end coupled to said tissue grasper assembly proximal to the distal end of said collar and configured to be moved longitudinally, while the distal end of said controller remains coupled to said tissue grasper assembly proximal to the distal end of said collar, to move said one or more grasper arms between the closed configuration and the open configuration;

wherein:

each of said one or more grasper arms has a first end coupled to the distal end of said collar and extends proximally to a free end positioned adjacent said collar when in the closed configuration and transversely away from said collar when in the open configuration;

at least one of said one or more grasper arms has a grasper surface facing said collar when said at least one of said one or more grasper arms is in the closed configuration to hold body tissue between said grasper surface and said collar with the body tissue contacting an outer surface of said collar as well as said grasper surface;

a grasping feature extends transverse to said grasper surface and is shaped and configured, and structurally differentiated from said grasper surface to hold body tissue with respect to said grasper surface; and said tissue grasper assembly is separable from said shaft and said controller to remain deployed grasping body tissue.

2. The tissue manipulating device of claim 1, wherein said one or more grasper arms are pivotably coupled to said collar.

3. The tissue-manipulating device of claim 1, wherein said tissue grasper assembly comprises a locking feature engageable to hold said one or more grasper arms in one of the closed configuration or the open configuration when said tissue grasper assembly is separated from said shaft and said controller.

4. The tissue-manipulating device of claim 1, further comprising a controller coupling coupled between said one or more grasper arms and said controller and movable upon actuation of said controller to move said one or more grasper arms between the closed configuration and the open configuration.

5. The tissue manipulating device of claim 1, wherein said tissue grasper assembly is removably coupled to said shaft via said collar.

6. The tissue-manipulating device of claim 1, further comprising a controller coupling, wherein said collar and said controller coupling comprise interengaging locking features configured to hold said controller coupling in place to hold said one or more grasper arms in the closed configuration.

7. The tissue-manipulating device of claim 1, wherein said one or more grasper arms have blunt ends extending away from the distal end of said shaft.

8. The tissue-manipulating device of claim 1, further comprising a controller coupling, wherein said controller coupling comprises a plurality of linkage arms coupled to move said one or more grasper arms between the closed configuration and the open configuration.

9. The tissue-manipulating device of claim 8, wherein said controller coupling comprises at least two controller elements coupled to respective first and second grasper arms to independently control said first and second grasper arms.

10. A tissue manipulating device comprising:

a shaft;

a collar coupled to a distal end of said shaft;

a tissue grasper assembly coupled to a distal end of said collar and comprising one or more grasper arms movable between a closed configuration extending along said collar and an open configuration extending away from said collar; and a controller having a distal end coupled to said tissue grasper assembly proximal to the distal end of said collar and configured to be moved longitudinally, while the distal end of said controller remains coupled to said tissue grasper assembly proximal to the distal end of said collar, to move said one or more grasper arms between the closed configuration and the open configuration;

wherein:

each of said one or more grasper arms has a first end coupled to the distal end of said collar and extends proximally to a free end positioned adjacent said collar when in the closed configuration and transversely away from said collar when in the open configuration;

at least one of said one or more grasper arms has a grasper surface facing said collar when said at least one of said one or more grasper arms is in the closed configuration to hold body tissue between said grasper surface and said collar with the body tissue contacting an outer surface of said collar as well as said grasper surface; and a grasping feature extends transverse to said grasper surface and is shaped and configured, and structurally differentiated from said grasper surface to hold body tissue with respect to said grasper surface; and said tissue grasper assembly is removably coupled to said shaft via said collar.

11. The tissue manipulating device of claim 10, wherein said one or more grasper arms are pivotably coupled to said collar.

12. The tissue manipulating device of claim 10, wherein said tissue grasper assembly comprises a locking feature engageable to hold said one or more grasper arms in one of the closed configuration or the open configuration when said tissue grasper assembly is separated from said shaft and said controller.

13. The tissue manipulating device of claim 10, further comprising a controller coupling coupled between said one or more grasper arms and said controller and movable upon actuation of said controller to move said one or more grasper arms between the closed configuration and the open configuration.

14. The tissue manipulating device of claim 10, further comprising a controller coupling, wherein said collar and said controller coupling comprise interengaging locking features configured to hold said controller coupling in place to hold said one or more grasper arms in the closed configuration.

15. The tissue-manipulating device of claim 10, wherein said one or more grasper arms have blunt ends extending away from the distal end of said shaft.

16. A tissue manipulating device comprising: a shaft; a collar coupled to a distal end of said shaft; a tissue grasper assembly coupled to a distal end of said collar and comprising one or more grasper arms movable between a closed configuration extending along said collar and an open configuration extending away from said collar; and a controller having a distal end coupled to said tissue grasper assembly proximal to the distal end of said collar and configured to be moved longitudinally, while the distal end of said controller remains coupled to said tissue grasper assembly proximal to the distal end of said collar, to move said one or more grasper arms between the closed configuration and the open configuration; wherein:

each of said one or more grasper arms has a first end coupled to the distal end of said collar and extends proximally to a free end positioned adjacent said collar when in the closed configuration and transversely away from said collar when in the open configuration; at least one of said one or more grasper arms has a grasper surface facing said collar when said at least one of said one or more grasper arms is in the closed configuration to hold body tissue between said grasper surface and said collar with the body tissue contacting an outer surface of said collar as well as said grasper surface; a grasping feature extends transverse to said grasper surface and is shaped and configured, and structurally differentiated from said grasper surface to hold body tissue with respect to said grasper surface; and a controller coupling comprising a plurality of linkage arms coupled to move said one or more grasper arms between the closed configuration and the open configuration.

17. The tissue-manipulating device of claim 16, wherein said tissue grasper assembly comprises a locking feature engageable to hold said one or more grasper arms in one of the closed configuration or the open configuration.

18. The tissue-manipulating device of claim 16, wherein said controller coupling comprises at least two controller elements coupled to respective first and second grasper arms to independently control said first and second grasper arms.

19. The tissue manipulating device of claim 16, wherein said one or more grasper arms are pivotably coupled to said collar.

20. The tissue manipulating device of claim 16, wherein said collar and said controller coupling comprise interengaging locking features configured to hold said controller coupling in place to hold said one or more grasper arms in the closed configuration.

* * * * *